United States Patent [19]

Lo et al.

[11] 4,221,716
[45] Sep. 9, 1980

[54] INTERMEDIATE AND PROCESS FOR THE PREPARATION OF 7-ACYLINDOLIN-2-ONES

[75] Inventors: Young S. Lo; David A. Walsh; William J. Welstead, Jr., all of Richmond, Va.

[73] Assignee: A. H. Robins Company, Inc., Richmond, Va.

[21] Appl. No.: 12,698

[22] Filed: Feb. 16, 1979

[51] Int. Cl.² .................. C07D 209/34; C07D 209/08
[52] U.S. Cl. ............................. 260/325 R; 260/326.16
[58] Field of Search ....................... 260/325 R, 326.16

[56] References Cited

PUBLICATIONS

T. Sugasawa et al., JACS, 100:15, pp. 4842–4852 (1978).
E. Pratt et al., JOC, 29, pp. 1540–1543 (1964).
J. Powers, JOC, 31, pp. 2627–2631 (1966).
W. Lawson et al., JACS. 82, p. 5918 (1960).
V. W. Houlihan, Indoles, Part I, pp. 77, 115, 116. Wiley & Sons, NY (1972).

*Primary Examiner*—Donald G. Daus
*Assistant Examiner*—M. C. Eakin

[57] ABSTRACT

A novel process for the preparation of 7-acylindolin-2-ones of the formula:

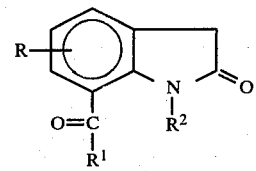

wherein R is hydrogen, halogen, lower alkyl, lower alkoxy, or trifluoromethyl; $R^1$ is lower alkyl, alkylphenyl, cycloalkyl, or aryl; and $R^2$ is hydrogen, lower alkyl or benzyl is provided. The compounds are useful as intermediates in the preparation of 2-amino-3-acylphenylacetic acid compounds which possess pharmaceutical properties.

14 Claims, No Drawings

INTERMEDIATE AND PROCESS FOR THE PREPARATION OF 7-ACYLINDOLIN-2-ONES

This invention provides a novel process for the preparation of 7-acylindolin-2-ones of the formula:

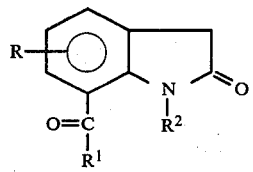

wherein R is hydrogen, halogen, lower alkyl, lower alkoxy, or trifluoromethyl; $R^1$ is lower alkyl, alkylphenyl, cycloalkyl, or aryl; and $R^2$ is hydrogen, lower alkyl or benzyl.

The 7-acylindolin-2-ones are prepared by the following sequence of steps: (1) acylating an indoline with a nitrile in the presence of boron trichloride and aluminum trichloride to produce a 7-acylindoline; (2) dehydrogenating the 7-acylindoline to produce a 7-acylindole; (3) halogenating the 7-acylindole to produce a 7-acyl-3-halo-indole; and (4) hydrolyzing the 7-acyl-3-halo-indole with phosphoric acid to produce a 7-acylindolin-2-one. When 7-acylindolin-2-ones are prepared wherein $R^2$ is other than hydrogen, it is necessary to alkylate the 7-acylindoline obtained in step (1), preferably with sodium hydride and lower alkyl halide or benzyl halide prior to proceeding to the dehydrogenation of the 7-acylindoline according to step (2) above.

Preferably, 7-benzoylindolin-2-ones are prepared by the process of this invention. These compounds are useful as intermediates in the preparation of 2-amino-3-benzoylphenylacetic acids and esters, salts and hydrates thereof which possess valuable pharmaceutical properties.

BACKGROUND OF THE INVENTION

The 7-acylindolin-2-ones prepared by the process of this invention are useful in the preparation of 2-amino-3-acylphenylacetic acids and esters, salts and hydrates thereof. Preferably, the novel process of this invention is used in the preparation of 7-benzoylindolin-2-ones. The 7-benzoylindolin-2-ones are intermediates in a novel route to produce 2-amino-3-benzoylphenylacetic acids starting with indoline or 4-, 5- or 6-substituted indolines. The reaction sequence of this route is indolines→7-benzoylindolines→7-benzoylindoles→7-benzoyl-3-halo-indoles→7-benzoylindolin-2-ones→2-amino-3-benzoylphenylacetic acids. The 2-amino-3-benzoylphenylacetic acids are disclosed in U.S. Pat. Nos. 4,045,576 and 4,126,635. These compounds possess valuable pharmacological properties and are useful as pharmaceutical agents. They particularly exhibit excellent anti-inflammatory activity.

U.S. Pat. Nos. 4,045,576 and 4,126,635 disclose methods for the preparation of 7-benzoylindolin-2-ones. According to one method, 1-aminoindolin-2-one is reacted with a phenylacetone to give a 1-(α-methylphenethylindenimino) indolin-2-one which is cyclized in ethanolic hydrogen chloride to an ethyl α-(2-methyl-3-phenylindol-7-yl)acetate. This indolylester is treated with ozone in acetic acid solution to give an ethyl 2-acetamido-3-benzoylphenylacetate which is hydrolyzed and cyclized in dilute mineral acid to a 7-benzoylindolin-2-one.

Alternatively, these patents disclose that an ethyl α-(2-methyl-3-phenylindol-7-yl)acetate may be hydrolyzed in aqueous basic solution to an α-(2-methyl-3-phenylindol-7-yl) acetic acid which is treated with ozone in acetic acid solution to give a 2-acetamido-3-benzoylphenylacetic acid. The acid is hydrolyzed and cyclized in dilute acid to the 7-benzoylindolin-2-one.

U.S. Pat. No. 3,897,451 also discloses a method of preparing indolin-2-ones. Under this procedure, N-chloro-aniline is reacted with β-thiocarboxylic ester to form an azasulfonium salt which is treated with a substantially anhydrous base to form an ortho-[(thioalkyl)-(alkylthiocarbonyl)methyl]aniline. This ortho-substituted aniline is heated or acidified to form 3-thioalkyl-indolin-2-one which is desulfurized to form the indolin-2-one.

U.S. Pat. No. 3,975,531 discloses the preparation of 7-benzoylindolin-2-ones by (a) cyclization of 2-acetamido-3-benzoylphenylacetic acid or ethyl 2-acetamido-3-benzoylphenylacetate or (b) by reacting aminobenzophenones with alkyl α-(methylthio)acetates to give alkyl 2-amino-3-benzoyl-α-(methylthio)phenylacetates which are then cyclized and demethylthiolated to produce the 7-benzoylindolin-2-one.

These prior art methods are suitable for use in the preparation of 7-benzoylindolin-2-ones. However, these methods either produce low yields or must be conducted at low temperatures making them undesirable for large scale operation.

It is an object of this invention to provide novel methods for the preparation of 7-acylindolines, 7-acyl-3-halo-indoles and 7-acylindolin-2-ones.

It is a further object of this invention to provide novel 7-acylindoles and 7-acyl-3-halo-indoles.

Additional objects will be apparent to one skilled in the art and still other objects will become apparent hereinafter from the following description of invention, the best mode of carrying out the invention, and the examples thereof.

DESCRIPTION OF THE INVENTION

One or more objects of the present invention are accomplished by the provision of a novel method for the preparation of 7-acylindolin-2-ones of the formula:

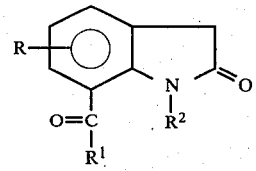

wherein R is hydrogen, halogen, lower alkyl, loweralkoxy or trifluoromethyl; $R^1$ is lower alkyl, alkylphenyl, cycloalkyl, or aryl; and $R^2$ is hydrogen, lower alkyl, or benzyl.

The 7-acylindolin-2-ones are prepared by a novel method comprising the following sequence of steps:

(1) acylating an indoline of the formula

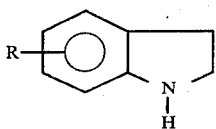

wherein R is as given above, with a nitrile of the formula

R¹CN wherein R¹ is as given above, in the presence of boron trichloride and aluminum trichloride to produce a 7-acylindoline of the formula

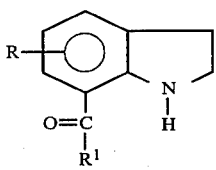

wherein R and R¹ are as given above, with the provision that where R² is other than hydrogen the 7-acylindoline is alkylated to obtain the desired substitution on the nitrogen, preferbly with sodium hydride and lower alkyl halide or benzyl halide;

(2) dehydrogenating the 7-acylindoline product obtained in step (1) to produce a 7-acylindole of the formula

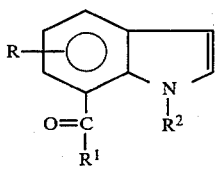

wherein R, R¹ and R² are as given above;

(3) halogenating the 7-acylindole product obtained in step (2) to produce a 7-acyl-3-halo-indole of the formula

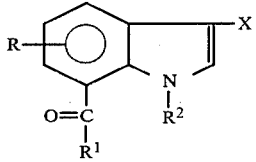

wherein R, R¹ and R² are as given above and X is halogen; and (4) hydrolyzing the 7-acyl-3-halo-indole product obtained in step (3) with phosphoric acid to produce the desired 7-acylindolin-2-one as described above.

The 2-amino-3-acylphenylacetic acid compounds mentioned above have the formula

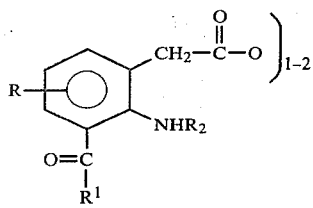

wherein R, R¹ and R² are as given above, and R³ is hydrogen, lower alkyl, or metal cation. These compounds may be prepared by the hydrolysis of 7-acylindolin-2-ones in aqueous basic solution to provide salts thereof which may be acidified to obtain the acid. To obtain the lower alkyl esters thereof, the acid is converted to a metal salt which is then reacted in a suitable solvent with an alkyl halide to furnish the desired ester.

In the definition of symbols in the formulas hereof and where they appear elsewhere throughout this specification, the terms have the following significance.

The term "lower alkyl" as used herein includes straight and branched chain radicals of up to six carbon atoms, preferably no more than four carbon atoms, and may be illustrated by such groups as methyl, ethyl, propyl, isopropyl, butyl, sec. butyl, tertiary butyl, amyl, isoamyl and hexyl. The term "lower alkoxy" has the formula —O-lower alkyl.

Preferably, the metal cation will be lithium, sodium, potassium, calcium, magnesium, aluminum, zinc or copper. Most preferably, the metal cation will be sodium or potassium.

The term "halogen" as used herein includes fluorine, chlorine, bromine, and iodine. Preferably, the halogen used is chlorine or bromine.

The term "aryl" as used herein refers to the phenyl radical or to a phenyl radical substituted by any radical or radicals which are not reactive or otherwise interfering under the conditions of reaction.

The term "cycloalkyl" as used herein refers to cyclic radicals having from three to seven carbon atoms and includes cyclopropyl, cyclobutyl, cyclopentyl, methylcyclopentyl, cyclohexyl, cycloheptyl, and the like.

The radical designated as R in the formulas of compounds prepared in accordance with the process of this invention includes single or multiple substitution on the ring wherever indicated.

The reaction sequence of the novel process of this invention may be illustrated as follows:

Step 1

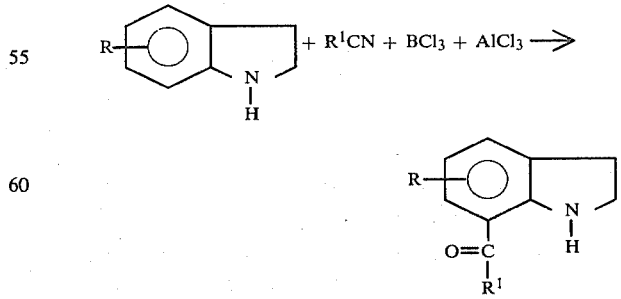

The indoline starting material is acylated with an appropriate nitrile in the presence of boron trichloride and aluminum trichloride under anhydrous conditions to obtain 7-acylindoline. The reaction is carried out in the presence of a suitable inert solvent such as toluene, benzene, dichloromethane, trichloromethane, chloroform, carbon tetrachloride, chlorobenzene, tetrachloroethane, xylene, or the like. Approximately equimolar amounts of the reactants are reacted preferably at a temperature of 80° C.–200° C.

Whenever the substituent on the nitrogen is desired to be lower alkyl or benzyl rather than hydrogen as shown above, the 7-acylindoline is alkylated, preferably with sodium hydride and a lower alkyl halide or benzyl halide in the presence of an inert solvent, such as dimethylformamide or dimethylsulfoxide, to obtain the desired substituent on the nitrogen.

The formation of 2-aminophenylketones by the reactions of anilines and nitriles in the presence of boron trichloride and aluminum trichloride is disclosed and described in T. Sugasawa, et al., J. Amer. Chem. Soc. 100, 4842 (1978). Step (1) of the present invention illustrates that an ortho substitution reaction assisted by boron trichloride and aluminum trichloride may be carried out on polycyclic compounds such as the indoline starting materials of this invention.

The indoline starting materials of this invention may be conveniently prepared by known methods.

Step 2

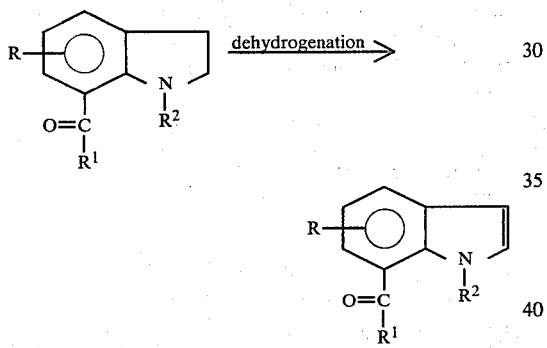

The 7-acylindoline product obtained in step (1) is dehydrogenated to produce the corresponding 7-acylindole compound. These indole derivatives as prepared herein are novel compounds. This reaction may be carried out by dehydrogenation of the 7-acylindoline with manganese dioxide or in the presence of a suitable catalyst such as a noble metal (i.e., palladium, ruthenium, rhodium, osmium, iridium and platinum on charcoal or Raney nickel, in an inert solvent, such as toluene, benzene, chlorobenzene or the like, with or without a hydrogen acceptor, such as cinnamic acid, maintained at 100°–200° C. for 1–100 hours. Preferably, under step (2) of the present invention, the 7-acylindoline is dehydrogenated using 1 to 5 molar equivalents of manganese dioxide in the presence of an inert solvent under reflux for a period of about 1 to 24 hours depending upon temperature used.

Methods of dehydrogenating indoline derivatives to produce indole derivatives are disclosed and described in "The Chemistry of Indoles," by Richard J. Sundberg, 1970, and "Indoles, Part I and Part II," edited by William J. Houlihan, 1972.

Catalytic dehydrogenation effected by a noble metal catalyst on charcoal in an aromatic solvent with a hydrogen acceptor was disclosed in S. Sugasawa et al., J. Pharm. Soc. Jap. 58, 139 (1938). The oxidation of indolines to produce the corresponding indole using manganese dioxide is disclosed and described in E. F. Pratt et al., J. Org. Chem. 29, 1540 (1964).

Step 3

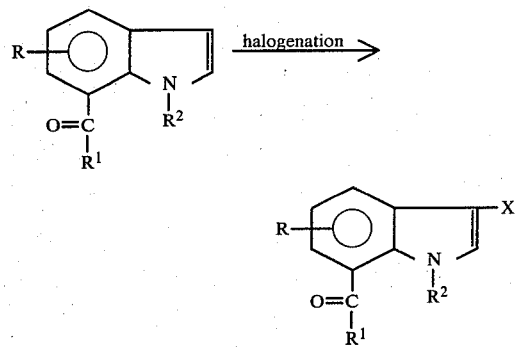

The novel 7-acylindole product obtained from step (2) is halogenated to produce novel 7-acyl-3-halo-indoles using an appropriate halogenation agent, such as N-chlorosuccinimide, N-bromosuccinimide, chlorine gas, calcium hypochlorite, sodium hypochlorite, tert.-butyl hypochlorite, trichloroisocyanuric acid and the like. Preferably the agent used is N-chlorosuccinimide.

The 7-acylindole dissolved in an organic inert solvent, such as methylene chloride, is reacted with the halogenation agent, preferably N-chlorosuccinimide, under a nitrogen atmosphere at a temperature maintained between 0°–100° C. for a period of about 3 hours until the halogenation reaction is complete.

The Sundberg and Houlihan references cited hereinbefore disclosed and describe broadly the halogenation of indole derivatives utilizing the halogenation agents useful for the purposes of this invention. However, these references do not discose the halogenation of the 7-acylindoles of this invention.

Step 4

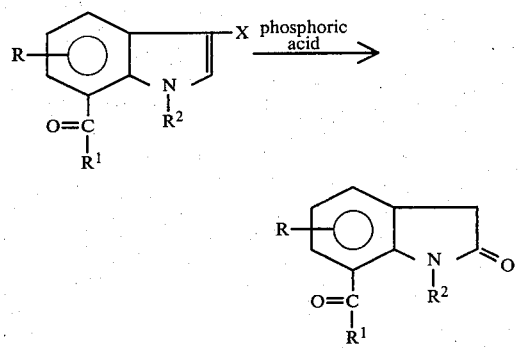

The novel 7-acyl-3-halo-indole product obtained from step (3) is hydrolyzed with phosphoric acid while dissolved in solvent, such as 2-methoxy-ethanol or acetic acid, to produce 7-acylindolin-2-one. This hydrolysis reaction is carried out under reflux for a period of from about 4–24 hours until the reaction is complete.

The Sundberg and Houlihan references discussed hereinbefore disclose and describe the mechanism of hydrolysis of 3-halo-indoles to their corresponding indolin-2-ones. The use of hydrochloric acid to cause such hydrolysis is disclosed in J. C. Powers, J. Org. Chem. 31, 2627 (1966) and the use of sulfuric acid to cause such hydrolysis is disclosed in W. B. Lawson et al., J. Amer. Chem. Soc. 82, 5918 (1960).

The use of phosphoric acid in such hydrolysis was not known prior to its use in the process of this invention. Attempts to prepare 7-benzoylindolin-2-ones from 7-benzoyl-3-halo-indoles using sulfuric acid or hydrochloric acid as suggested by the prior disclosures discussed above resulted in excessive reaction time and products having extremely high tar contents.

The 7-acylindolin-2-ones prepared by the process of this invention may be converted by hydrolysis to obtain 2-amino-3-acylphenylacetic acids and esters, salts and hydrates thereof. The 2-amino-3-benzoylphenylacetic acid compounds possess valuable pharmacological properties and are useful as pharmaceutical agents.

The process of this invention is carried out in a number of reaction steps each producing valuable intermediate products. These products may be isolated individually upon the completion of a particular step or the process may be carried out in a continuous manner in which the 7-acylindolin-2-ones or the 2-amino-3-acylphenylacetic acid products may be produced in a continous reaction from the indoline starting materials.

The products obtained by the reaction procedures described in steps 2 and 3 as indicated above are novel compounds which may be represented by the following formula:

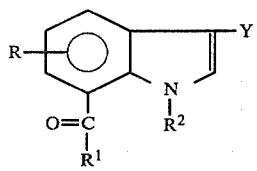

wherein R, $R^1$ and $R^2$ are as given above, and Y is hydrogen or halogen.

The following examples are further illustrative of the present invention. The reactants and other specific ingredients are presented as being the best mode of carrying out the invention, and various modifications can be devised in view of the foregoing disclosure within the scope of the invention.

EXAMPLE 1

This example illustrates the preparation of 7-benzoylindoline from indoline.

One mole of indoline, 1.2 moles of benzonitrile and 555 ml of toluene are combined in a reaction vessel and heated at reflux until 90 ml of toluene has been distilled to remove any moisture present.

A separate reaction vessel is charged with 745 ml of toluene. The toluene is chilled to 5° C. and 1.1 moles of boron trichloride is added to the toluene. The resulting solution is maintained at 5°–10° C. while the dried indoline-benzonitrile solution is added thereto over a period of 2.5 hours. While this solution is maintained at 5°–10° C., 1.1 moles of aluminum chloride are added over a period of 45 minutes.

The reaction vessel containing the above solution is then transferred to a heating mantle and slowly heated to reflux while providing for adequate venting or scrubbing of the resulting gases. The solution is allowed to reflux for a period of 16 hours, then cooled to 8° C. and 188 ml of water is added to decompose the excess aluminum chloride. The reaction mixture is then charged with 800 ml of 2 N hydrochloric acid and heated at reflux for 2.5 hours. During the reflux period the mixture changes to a tan, granular suspension. The mixture is allowed to cool over night and then filtered. The collected solid is washed several times with ice water and compressed with rubber sheeting. The damp solid obtained is resuspended in 1100 ml of water maintained at a temperature below 20° C. and basified with 25% sodium hydroxide. The resulting suspension changes to a yellow, granular consistency and, upon stirring for a 4-hour period, becomes milky and the solid loses its granular appearance. The resulting yellow solid is collected and compressed with rubber sheeting. The damp solid is resuspended in water for 0.5 hour and filtered. The 7-benzoylindoline product is dried at 125° F./26 in Hg vacuum (air bleed), yielding a product having a melting range of 121°–125° C.

EXAMPLE 2

This example illustrates the preparation of 7-benzoylindole from 7-benzoylindoline.

A reaction vessel is charged with 2.23 liters of methylene chloride to which is added one mole of the 7-benzoylindoline obtained in Example 1. To this mixture is added 3.0 moles of activated manganese dioxide. This reaction mixture is agitated and heated at reflux for 24 hours to produce 7-benzoylindole. The produce is then filtered through a filter that will retain the manganese dioxide. The reaction vessel is rinsed with 0.2 liter of hot methylene chloride and the filter cake washed with this rinse. The 7-benzoylindole product obtained has a melting point of 100°–104.5° C.

EXAMPLE 3

This example illustrates the preparation of 7-benzoyl-3-chloro-indole from 7-benzoyl-indole.

The 7-benzoylindole product (approximately 0.87 mole) in methylene chloride (the reaction mixture obtained in Example 2) is agitated and chilled to 15° C. in a nitrogen atmosphere. N-Chlorosuccinimide (0.87 mole) (NCS) is divided into four equal portions and added to the 7-benzoylindole-methylene chloride mixture at one-half hour intervals while maintaining the reaction temperature between 15°–20° C. One hour after the addition of the final portion of N-chlorosuccinimide, the succinimide is washed from the reaction by adding approximately 2.5 liters of water to the reaction mixture, agitating for about 15 minutes and then allowing the resulting layers to separate. The lower methylene chloride layer is drawn into another vessel and washed again with about 2.5 liters of water. The two aqueous portions are combined and extracted with about 0.2 liters of methylene chloride. This methylene chloride solution is washed with an equal volume of water. The two methylene chloride solutions are combined and distilled at a reduced pressure to a liquid temperature of approximately 80° C. The 7-benzoyl-3-chloro-indole residue obtained has a melting range of 145°–149° C.

EXAMPLE 3(a)

This example illustrates the preparation of 3-bromo-7-benzoylindole from 7-benzoylindole.

To a solution of 22.1 grams (0.1 mole) of 7-benzoylindole in 155 ml of methylene chloride cooled and maintained at a temperature of about 20° C. was added 18.7 grams (0.105 mol) of N-bromosuccinimide in four equal portions over a period of 1 hour. The mixture was then washed with two portions of 200 ml of water. The organic fraction was separated, dried and concentrated to obtain 28.7 grams of product. A portion of this product was recrystallized from 95% ethanol to obtain a product having a m.p. of 145°–147° C.

Analysis: Calculated for $C_{15}H_{10}NOBr$: C, 60.02; H, 3.36; N, 4.67; Found: C, 59.71; H, 3.45; N, 4.66.

EXAMPLE 4

This example illustrates the preparation of 7-benzoyl-indolin-2-one from 7-benzoyl-3-chloro-indole.

The 7-benzoyl-3-chloro-indole (the product obtained in Example 3, 0.87 mole) was dissolved in 1.8 liters of 2-methoxy-ethanol and heated to 100° C. with agitation. To this reaction mixture was added 1.3 liters of 70% phosphoric acid solution in a steady stream. The resulting indole phosphate salt separates at this point. The agitation is continued and the reaction brought to reflux temperature. This hydrolysis reaction takes about 4–8 hours. The reaction color is red and a small amount of polymeric residue is present.

Once the reaction had gone to completion, the reaction mixture was treated with charcoal and vacuum or pressure filtered through an appropriate filter bed. The filtrate obtained was drawn into a crystalling vessel and the temperature adjusted to about 70° C. The reaction mixture was stirred at 65°–70° C. and 2.3 liters of water added thereto. The product began to crystallize during the water addition. The resulting slurry was slowly cooled to about 5° C. and held at that temperature for about 12 hours. The 7-benzoylindolin-2- one product was collected on a filter and dried in a vacuum oven at about 65° C. This product had a melting range of 146°–151° C.

EXAMPLE 5

This example illustrates the preparation of sodium-2-amino-3-benzoylphenylacetate hydrate from 7-benzoylindolin-2-one.

One mole of 7-benzoylindolin-2-one is added with stirring to a reaction vessel containing 0.711 liter of toluene and 0.711 liter of 95% ethanol. The reaction mixture was heated at 70° C. under nitrogen until the 7-benzoylindolin-2-one is dissolved. The heat is discontinued and 1.2 moles of 50% sodium hydroxide is added to the reaction mixture. After about three-fourths of the sodium hydroxide had been added, the sodium adduct of the 7-benzoylindolin-2-one came out of solution as a heavy precipitate. Once the sodium hydroxide had been completely added, the reaction mixture is brought to reflux. This hydrolysis reaction was complete in 4–5 hours.

The heating was discontinued and 14.7 grams of charcoal added to the reaction mixture. The mixture was returned to reflux for about 15 minutes. The mixture was then filtered through an appropriate filter bed. The resulting dark red filtrate was transferred to a crystallizing vessel and the filtrate was agitated while 1.422 liters of di-isopropyl ether was added to the filtrate. The 2-amino-3-benzoyl-phenylacetic acid salt began to crystallize immediately. The slurry was chilled to 5° C. and kept at that temperature for 7–8 hours. The product was collected by filtration and the filter cake was slowly washed with 0.05 liter of 1,2-dimethoxyethane that had been chilled to 5° C.

The sodium-2-amino-3-benzoylphenylacetate hydrate was vacuum-dried at about 65° C. This product had a melting point of between 235°–245° C.

The above examples show the preparation of a sodium salt of 2-amino-3-benzoylphenylacetic acid starting from indoline and going through intermediate compounds: 7-benzoylindoline; 7-benzoylindole; 7-benzoyl-3-chloroindole; and 7-benzoylindolin-2-one. The above examples cover the preferred preparation of this invention. It should be understood that various modifications can be devised in view of the foregoing disclosure within the scope of the invention. For example, an alkyl, alkoxy, halogen, or trifluoromethyl substituted indoline may be used as a starting material and following the same sequence of reactions produce the corresponding substituted 7-benzoyl-indolin-2-one and subsequently the corresponding substituted 2-amino-3-benzoylphenyl acetic acid or salt thereof.

EXAMPLE 6

This example illustrates the preparation of 1-methyl-7-benzoylindoline from 7-benzoylindoline.

To a stirred slurry of 4.8 grams (0.1 mole) of 50% sodium hydride/oil in 100 ml. of dimethylformamide is added dropwise a solution of 22.3 grams (0.1 mole) of 7-benzoylindoline in 50 ml of dimethylformamide. After addition is complete, the mixture is warmed at 50° C. until all solids dissolve. While maintaining the mixture at 50° C., 9.5 grams (0.1 mole) of methyl iodide is added dropwise to the mixture. The mixture is stirred for 4 hours. The mixture is poured into 2 liters of ice water and extracted with 3 portions of 300 ml of benzene. The benzene extracts are combined, washed with water, dried over sodium sulfate and concentrated to give 1-methyl-7-benzoylindoline as a residue.

EXAMPLE 6(a)

This example illustrates an alternate method for the preparation of 1-methyl-7-benzoylindoline from 7-benzoyl-indoline.

Twenty ml of glacial acetic acid was added dropwise to a solution of 22.3 grams (0.1 mole) of 7-benzoylindoline, 100 ml. of 37% formaldehyde, and 15.7 grams (0.25 mol) of sodium cyano borohydride in 300 ml of acetonitrile. The solution refluxed from the heat of reaction and was stirred overnight. An additional 25 ml of formaldehyde, 12 grams of sodium cyano borohydride and 10 ml of acetic acid were added to the solution following the procedure above and stirring was continued for 30 minutes. The solution was combined with 1 liter of ethyl ether and the mixture was extracted with 3 portions of 500 ml of 1 N sodium hydroxide. The organic fraction obtained was washed with salt water (brine), dried and concentrated to give 26 grams of product which was distilled to yield 20.5 grams of 1-methyl-7-benzoylindoline having a b.p. of 150° C./0.01 mm Hg.

Analysis: Calculated for $C_{16}H_{15}NO$: C, 80.98; H, 6.37; N, 5.90; Found: C, 80.96; H, 6.36; N, 6.03.

EXAMPLE 7

This example illustrates the preparation of 1-methyl-7-benzoylindole from 1-methyl-7-benzoylindoline.

A mixture of 2.4 grams (0.01 mole) of 1-methyl-7-benzoylindoline and 8.7 grams (0.1 mol) of manganese dioxide in 25 ml of methylene chloride was heated at reflux for 18 hours. The mixture was cooled and filtered. The filtrate was concentrated and the resulting residue was distilled to give 2 grams of 1-methyl-7-benzoylindole having a b.p. of 128° C./0.03 mm Hg.

Analysis: Calculated for $C_{16}H_{13}NO$: C, 81.68; H, 5.57; N, 5.95; Found: C, 81.40; H, 5.70; N, 6.08.

EXAMPLE 8

This example illustrates the preparation of 3-chloro-1-methyl-7-benzoylindole from 1-methyl-7-benzoylindole.

To a solution of 11.7 grams (0.05 mol) of 1-methyl-7-benzoylindole in 100 ml. of methylene chloride cooled to a temperature of 15° C. was added 6.7 grams (0.05 mol) of N-chlorosuccinimide in four equal portions over a period of 1 hour. The mixture was stirred for an additional 30 minutes, then extracted with two 50 ml portions of dilute sodium hydroxide solution followed by a water wash. The organic solution was dried with sodium sulfate and concentrated to give 13.5 grams of product. A portion of the product was recrystallized from 95% ethyl alcohol to obtain 3-chloro-1-methyl-7-benzoylindole having a m.p. of 73°–74.5° C.

Analysis: Calculated for $C_{16}H_{12}NOCl$: C, 71.25; H, 4.48; N, 5.19; Found: C, 71.01; H, 4.52; N, 5.16.

EXAMPLE 9

This example illustrates the preparation of 1-methyl-7-benzoylindolin-2-one from 3-chloro-1-methyl-7-benzoylindole.

A solution of 46 grams (0.17 mol) of 3-chloro-1-methyl-7-benzoylindole in 250 ml of methoxy-ethanol and 60 ml of 70% phosphoric acid was heated at reflux under a nitrogen atmosphere for 5 hours. The solution was then cooled and diluted with 1.5 liters of water. The organic materials were extracted with methylene chloride and concentrated. The concentrated extract was chromatographed on silica gel and the product eluted with isopropyl ether. The residue obtained crystallized upon standing and was recrystallized from isopropyl alcohol to give 8.9 grams of 1-methyl-7-benzoylindolin-2-one, having a m.p. of 89°–90.5° C.

Analysis: Calculated for $C_{16}H_{13}NO_2$: C, 76.48; H, 5.22; N, 5.57; Found: C, 76.74; H, 5.25; N, 5.63.

EXAMPLE 10

This example illustrates the preparation of 1-benzyl-7-benzoylindolin-2-one from 7-benzoylindoline.

The procedure disclosed in Examples 6–9 are repeated except 17.1 grams (0.1 mol) of benzyl bromide is substituted for the 9.5 grams (0.1 mol) of methyl iodide used in Example 6.

Various modifications and equivalents will be apparent to one skilled in the art and may be made in the compounds, compositions and methods of the present invention without departing from the spirit or scope thereof.

What is claimed is:

1. A process for the preparation of a 7-acylindolin-2-one of the formula:

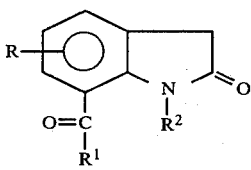

wherein R is selected from the group consisting of hydrogen, halogen, lower alkyl, lower alkoxy and trifluoromethyl; $R^1$ is selected from the group consisting of lower alkyl, alkylphenyl, cycloalkyl, and aryl; and $R^2$ is selected from the group consisting of hydrogen, lower alkyl and benzyl, which comprises:

(1) acylating an indoline of the formula

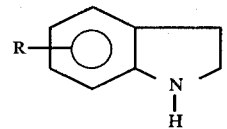

where R is as defined above with a nitrile of the formula $R^1CN$ wherein $R^1$ is as defined above in the presence of boron trichloride and aluminum trichloride to produce a 7-acylindoline of the formula:

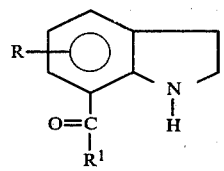

wherein R and $R^1$ are as defined above, with the provision that where $R^2$ is to be other than hydrogen the 7-acylindoline is alkylated to obtain the desired substitution on the nitrogen;

(2) dehydrogenating the 7-acylindoline obtained in step (1) to produce a 7-acylindole of the formula

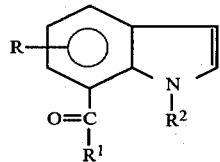

wherein R, $R^1$ and $R^2$ are as defined above;

(3) halogenating the 7-acylindole obtained in step (2) to produce a 7-acyl-3-halo-indole of the formula

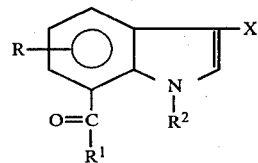

wherein R, $R^1$ and $R^2$ are as defined above and X is halogen; and (4) hydrolyzing the 7-acyl-3-halo-indole obtained in step (3) with phosphoric acid to produce a 7-acylindolin-2-one.

2. The process as defined in claim 1 wherein the 7-acylindolin-2-one is then hydrolyzed in aqueous base solution to produce a salt of 2-amino-3-acylphenylacetic acid.

3. The process as defined in claim 1 wherein a 7-benzoylindolin-2-one is prepared.

4. The process as defined in claim 3 wherein the 7-benzoylindolin-2-one is then hydrolyzed in aqueous basic solution to produce a salt of 2-amino-3-benzoylphenyl-acetic acid.

5. A process for the preparation of 7-benzoylindolin-2-one which comprises:
(1) acylating indoline with an equimolar amount of benzonitrile in an inert solvent under anhydrous conditions in the presence of boron trichloride and aluminum trichloride at a temperature of about 80°–200° C. to produce 7-benzoylindoline;
(2) dehydrogenating the 7-benzoylindoline produced in step (1) with 1 to 5 molar equivalents of manganese dioxide in the presence of an inert solvent at a reflux temperature to produce 7-benzoylindole;
(3) halogenating the 7-benzoylindole produced in step (2) with a halogenation agent in an organic inert solvent under a nitrogen atmosphere at a temperature maintained at about 0°–100° C. until the halogenation reaction is complete to produce 7-benzoyl-3-halo-indole; and
(4) hydrolyzing the 7-benzoyl-3-halo-indole produced in step (3) with phosphoric acid in a solvent at reflux temperatures to produce 7-benzoylindolin-2-one.

6. The process as defined in claim 5 wherein the 7-benzoylindolin-2-one is then hydrolyzed with aqueous sodium hydroxide to produce sodium 2-amino-3-benzoylphenylacetate hydrate.

7. A process for the preparation of a 7-acylindolin-2-one of the formula

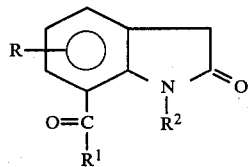

wherein R is selected from the group consisting of hydrogen, halogen lower alkyl, lower alkoxy and trifluoromethyl; $R^1$ is selected from the group consisting of lower alkyl, alkylphenyl, cycloalkyl and aryl; and $R^2$ is selected from the group consisting of hydrogen, lower alkyl and benzyl which comprises hydrolyzing a 7-acyl-3-halo-indole of the formula

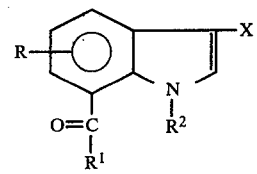

wherein R, $R^1$ and $R^2$ are as defined above and X is halogen with phosphoric acid.

8. The process as defined in claim 7 wherein 7-benzoyl-3-chloro-indole is hydrolyzed with phosphoric acid in a solvent at reflux temperature to produce 7-benzoylindolin-2-one.

9. A compound of the formula:

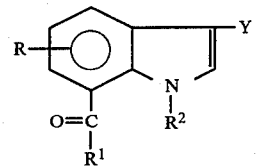

wherein R is selected from the group consisting of hydrogen, halogen lower alkyl, lower alkoxy and trifluoromethyl, $R^1$ is selected from the group consisting of lower alkyl, alkylphenyl, cycloalkyl and aryl; $R^2$ is selected from the group consisting of hydrogen, lower alkyl and benzyl; and Y is selected from the group consisting of hydrogen and halogen.

10. The compound of claim 9 which is 7-benzoylindole.

11. The compound of claim 9 which is 1-methyl-7-benzoylindole.

12. The compound of claim 9 which is 7-benzoyl-3-chloro-indole.

13. The compound of claim 9 which is 7-benzoyl-3-bromo-indole.

14. The compound of claim 9 which is 3-chloro-1-methyl-7-benzoylindole.

* * * * *